(12) United States Patent
Lantz

(10) Patent No.: US 12,207,920 B2
(45) Date of Patent: Jan. 28, 2025

(54) USER INTERFACE FOR AN AUDIOLOGICAL TEST SYSTEM

(71) Applicant: Natus Medical Incorporated, Pleasanton, CA (US)

(72) Inventor: Johannes Lantz, Malmö (SE)

(73) Assignee: Natus Medical Incorporated, Middleton, WI (US)

( * ) Notice: Subject to any disclaimer, the term of this patent is extended or adjusted under 35 U.S.C. 154(b) by 0 days.

(21) Appl. No.: 16/092,199

(22) PCT Filed: Mar. 6, 2018

(86) PCT No.: PCT/EP2018/055450
§ 371 (c)(1),
(2) Date: Nov. 1, 2019

(87) PCT Pub. No.: WO2018/162466
PCT Pub. Date: Sep. 13, 2018

(65) Prior Publication Data
US 2021/0267496 A1    Sep. 2, 2021

(30) Foreign Application Priority Data

Mar. 7, 2017   (EP) ..................................... 17159624

(51) Int. Cl.
*A61B 5/12* (2006.01)
*A61B 5/00* (2006.01)
(Continued)

(52) U.S. Cl.
CPC ............ *A61B 5/121* (2013.01); *A61B 5/6888* (2013.01); *A61B 5/7435* (2013.01);
(Continued)

(58) Field of Classification Search
CPC ..... A61B 5/121; A61B 5/6888; A61B 5/7435; A61B 5/7445; G06F 3/04817; G06F 3/1454; G06F 3/0488
See application file for complete search history.

(56) References Cited

U.S. PATENT DOCUMENTS

| 2002/0076056 A1* | 6/2002 | Pavlakos | A61B 5/411 381/60 |
| 2002/0165466 A1* | 11/2002 | Givens | A61B 5/12 600/559 |

(Continued)

*Primary Examiner* — William L Bashore
*Assistant Examiner* — Gregory A Distefano
(74) *Attorney, Agent, or Firm* — Daniel C. Pierron; Widerman Malek, PL

(57) ABSTRACT

A audiological test system is provided for audiological testing of a patient situated at a test location, comprising a first display screen for monitoring of the audiological test system and that is positioned outside a viewing field of the patient when the patient is situated at the test location, a second display screen positioned within the viewing field of the patient when the patient is situated at the test location, a first switch located at the first display screen and adapted for control of the second display screen in such a way that predetermined information relating to operation of the audiological test system is not displayed on the second display screen upon activation of the first switch, and a second switch located at the second display screen and adapted for control of the second display screen in such a way that the predetermined information relating to operation of the audiological test system is displayed on the second display screen upon activation of the second switch.

20 Claims, 16 Drawing Sheets

(51) Int. Cl.
  *G06F 3/04817* (2022.01)
  *G06F 3/0488* (2022.01)
  *G06F 3/14* (2006.01)
(52) U.S. Cl.
  CPC ........ *A61B 5/7445* (2013.01); *G06F 3/04817* (2013.01); *G06F 3/0488* (2013.01); *G06F 3/1454* (2013.01)

(56) References Cited

U.S. PATENT DOCUMENTS

| | | | | |
|---|---|---|---|---|
| 2004/0152998 A1* | 8/2004 | Stott | ...................... | A61B 5/742 600/559 |
| 2004/0212610 A1* | 10/2004 | Hamlin | ................. | G06F 3/1423 345/211 |
| 2005/0033193 A1* | 2/2005 | Wasden | ................. | A61B 5/121 600/559 |
| 2008/0034038 A1* | 2/2008 | Ciudad | ................ | G06Q 10/107 709/204 |
| 2008/0165080 A1* | 7/2008 | Reddy | ................... | G06F 1/1601 345/1.1 |
| 2012/0050260 A1* | 3/2012 | Cheng | ................... | G06F 3/1438 345/419 |
| 2012/0117156 A1* | 5/2012 | Anka | ...................... | H04N 7/15 709/205 |
| 2012/0284197 A1* | 11/2012 | Sitrick | ............... | G06Q 10/0631 705/301 |
| 2013/0120251 A1 | 5/2013 | Lee | | |
| 2014/0325432 A1 | 10/2014 | Frederickson | | |
| 2015/0154749 A1* | 6/2015 | Kyusojin | ............... | G16H 30/40 345/667 |
| 2016/0110152 A1* | 4/2016 | Choi | ................... | G06F 3/04817 345/2.3 |
| 2016/0119388 A1* | 4/2016 | Sitrick | ................. | H04L 65/403 715/753 |
| 2016/0330268 A1* | 11/2016 | Feng | ................... | H04L 65/4015 |

* cited by examiner

USER INTERFACE FOR AN AUDIOLOGICAL TEST SYSTEM

RELATED APPLICATIONS

This application claims priority under 35 U.S.C § 371 to PCT application No. PCT/EP2018/055450, filed Mar. 6, 2018, which claims the benefit of the European Patent Application No. 17159624.0 filed Mar. 7, 2017. The disclosure of those applications is incorporated herein as if set out in full.

BACKGROUND OF THE DISCLOSURE

Technical Field of the Disclosure

A new user interface for an audiological test system is provided, comprising a first and a second display screen.

The audiological test system is used to diagnose and manage a patient with an ear problem by performing various audiological tests of the hearing mechanism; typically these tests are performed in a sound booth.

Description of the Related Art

Recently, PC-based audiological test systems have gained widespread market penetration. Many hearing clinics have started using a touch screen next to the patient when performing audiological tests, e.g. in a sound booth. The touch screen is typically used for controlling the PC-based audiological test system and for presenting information to the patient. The PC itself is typically placed outside the sound booth or, in absence of the sound booth at a distance from the patient, with a computer screen placed outside the field of view of the patient.

The PC-based audiological test system is operated by a trained operator, and the operator performs at least some of the audiological tests sitting at a desk with the computer screen placed in the field of view of the operator and outside the field of view of the patient. Typically, tone and speech audiometry and hearing aid fitting are performed while the operator is sitting at the desk.

With today's PC-based audiological test system, the operator has to invoke the operating system of the PC, e.g. Windows®, to set the monitor mode of the PC; e.g. in order to operate the PC in the "duplicate monitor mode" wherein the touch screen at the patient and the computer screen display the same information in the same way, i.e. information displayed on the computer screen is copied and also displayed on the touch screen next to the patient. In this way, the operator is allowed to control the PC-based audiological test system from the touch screen next to the patient.

However, some audiological tests require that the patient does not receive any visual cues relating to the tests, e.g. during pure tone audiometry it is imperative that the patient does not receive any visual cues on when the operator presents a tone to the patient which is typically indicated on the computer screen.

Today, it is common practice for the operator to turn off the touch screen next to the patient to make certain that the patient does not receive any visual cues relating to the test.

In other audiological tests, e.g. a lip reading speech test, the operator may use the operating system of the PC, e.g. Windows®, to set the PC to operate in the "extended monitor mode" wherein the touch screen at the patient is used to show stimuli to the patient while the computer screen is used by the operator to control, e.g., an audiometer of the audiological test system.

Thus, with today's PC-based audiological test system, when the touch screen is alternatingly used for operator control of the system and for showing stimulus to the patient, the operator has to invoke the operating system of the PC, e.g. Windows®, to change between "duplicate monitor mode" for identical display on two screens and "extended monitor mode" for individual display on each of the two screens.

However, it is cumbersome and time consuming for the operator of an audiological test system to have to move away from the patient in order to select the correct monitor mode of the PC-based audiological test system. Time is wasted, the audiological test work flow is interrupted, communication with the patient may be interrupted, and the calm atmosphere that is desired during audiological testing may be disturbed.

SUMMARY OF THE DISCLOSURE

Thus, it is an object to provide an audiological test system with an improved user interface that facilitates control of two display screens that are placed with a mutual distance so that they cannot be viewed simultaneously from a test location used for audiological testing of a patient.

It is another object to provide an audiological test system that relieves the operator from the task of invoking an operating system of a processor of the audiological test system to control operation of two display screens.

The above and other objects are fulfilled by provision of an audiological test system for audiological testing of a patient situated at a test location, the audiological test system comprising a first display screen for monitoring of the audiological test system and that is positioned outside a viewing field of the patient when the patient is situated at the test location, a second display screen positioned within the viewing field of the patient when the patient is situated at the test location, a first switch located at the first display screen and adapted for control of the second display screen in such a way that predetermined information relating to operation of the audiological test system is not displayed on the second display screen upon activation of the first switch, and a second switch located at the second display screen and adapted for control of the second display screen in such a way that the predetermined information relating to operation of the audiological test system is displayed on the second display screen upon activation of the second switch.

The second switch may be adapted for control of the second display screen in such a way that the predetermined information relating to operation of the audiological test system is alternatingly displayed and not displayed on the second display screen upon activation of the second switch.

The first switch may be a conventional mechanical switch, such as a push button switch, e.g. mounted in a separate housing proximate the first display screen; or mounted in a housing of the first display screen, e.g. at one of the sides of the first display screen. Alternatively; or additionally, the first switch may be realized by an icon displayed on the first display screen and activated by positioning of a cursor on top of the icon and clicking on it using a mouse, a trackball, or a touchpad as is well-known in the art of computer interfaces.

Likewise, the second switch may be a conventional mechanical switch, such as a push button switch, e.g. mounted in a separate housing proximate the second display screen; or mounted in a housing of the second display screen, e.g. at one of the sides of the second display screen. Alternatively; or additionally, the second switch may be realized by an icon displayed on the second display screen and activated by positioning a cursor on top of the icon and clicking on it using a mouse, a trackball, or a touchpad as is well-known in the art of computer interfaces.

The first display screen may be a first touch screen.

The first switch may be constituted by a specific touch sensitive area of the first touch screen, e.g. indicated by display of a specific icon at the specific touch sensitive area, and activated by pressing on the specific touch sensitive area with a finger or a stylus.

The second display screen may be a second touch screen.

The second switch may be constituted by a specific touch sensitive area of the second touch screen, e.g. indicated by display of a specific icon at the specific touch sensitive area, and activated by pressing on the specific touch sensitive area with a finger or a stylus.

The first and second switches may of the same type; or may be of different types.

The first switch may accommodate an indicator for indication of whether the predetermined information relating to operation of the audiological test system is displayed and not displayed on the second display screen.

For example, the operator of the audiological test system may press the second switch at the second display screen to duplicate the entire display of the first display screen on the second display screen and thereby allowing the operator to control the audiological test system from a position next to the patient.

The audiological test system may include equipment for performing one of, some of, or all of the following audiological tests and patient related applications: pure tone audiometry, speech audiometry, Bekesy Audiometry, tympanometry, ipsi and contra acoustic reflex measurements, otoacoustic emission measurements, lip reading test, measurement of ability to discriminate between different sound intensities, recognize pitch, distinguish speech from background noise, evoked potential measurements, e.g. auditory brainstem response audiometry, cortical response audiometry, auditory steady state response audiometry, wideband acoustic immittance measurements, probe microphone measurements, e.g. for in-situ hearing aid verification, hearing aid fitting, etc., hearing counselling and education applications, tinnitus assessment of pitch, loudness and maskability, and filling out questionnaires and interview forms on the screen.

The audiological test system may comprise a processor that is adapted to individually control the first and second display screens.

The processor may be adapted to control special purpose audiological test apparatuses with the required measurement circuitry and devices for performing the audiological tests.

The processor may be adapted for recording of results of the audiological tests.

The processor may form part of a computer, such as a PC, a laptop computer, a tablet computer, a PDA, a smartphone, a dedicated audiological device, such as a stand-alone audiometer, etc., etc.

For example, in a PC-based audiological test system with a Windows® operating system, the operating system of the processor is set to the "extended monitor mode" whereby the processor is adapted to individually control the first and second display screens.

In this way, the processor is adapted to selectively control, e.g. in response to operator input and/or during performance of selected audiological tests, the first and second display screens so that they display the same information in the same way, i.e. what is displayed on the first display screen is copied or moved to be displayed on the second display screen next to the patient, and optionally allow the operator to control the audiological test system from the location of the second display screen, e.g. a touch screen, next to the patient.

The processor is further adapted to selectively control the second display screen at the patient to show stimuli to the patient, e.g. during a lip reading test, while controlling the first display screen to be used for control of the audiological test system by the operator.

For example, during pure tone audiometry, the processor may be adapted to indicate on the first display screen only when the operator presents a tone to the patient.

With the new audiological test system, the operator is relieved from the task of turning off the second display screen next to the patient to make sure that the patient does not receive any visual cues relating to the audiological test.

With the new audiological test system, the operator is relieved from the task of invoking the operating system of the processor of the audiological test system to ensure proper control of the first and second display screens.

For example when the new audiological test system is PC-based, e.g. with a Windows® operating system, the PC operates in the "extended monitor mode" when audiological tests are performed and the audiological test software executed when the audiological tests are performed duplicates or moves the screen layout as required so that the first display screen and the second display screen present identical information when required, or the second display screen alone presents the information to the operator of the audiological test system when needed and controls the first and second display screens individually when needed.

The processor of the audiological test system may be adapted to display desired visual cues, control panels, counselling tools, etc. in individual windows that are automatically opened and closed on the second display screen as needed, e.g. as the audiological test progresses and/or based on navigation by the operator on the first display screen or on the second display screen and/or based on activation of the first and second switches.

As used herein, the terms "processor", "central processor", "signal processor", "controller", "system", etc., are intended to refer to CPU-related entities, either hardware, a combination of hardware and software, software, or software in execution.

For example, a "processor", "signal processor", "controller", "system", etc., may be, but is not limited to being, a process running on a processor, a processor, an object, an executable file, a thread of execution, and/or a program.

By way of illustration, the terms "processor", "central processor", "signal processor", "controller", "system", etc., designate both an application running on a processor and a hardware processor. One or more "processors", "central processors", "signal processors", "controllers", "systems" and the like, or any combination hereof, may reside within a process and/or thread of execution, and one or more "processors", "central processors", "signal processors", "controllers", "systems", etc., or any combination hereof, may be localized in one hardware processor, possibly in combination with other hardware circuitry, and/or distributed between two or more hardware processors, possibly in combination with other hardware circuitry.

Also, a processor (or similar terms) may be any component or any combination of components that is capable of performing data processing. For examples, the processor may be an ASIC processor, a FPGA processor, a general purpose processor, a microprocessor, a circuit component, or an integrated circuit.

BRIEF DESCRIPTION OF THE DRAWINGS

The drawings illustrate the design and utility of embodiments, in which similar elements are referred to by common reference numerals. These drawings may or may not be drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

In the drawings:

FIGS. 13A-16B show various exemplary screen dumps of the first display screen and the second display screen of the new audiological test system.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various illustrative examples of use of the new audiological test system according to the appended claims will now be described more fully hereinafter with reference to the accompanying drawings, in which various embodiments of new audiological test system are illustrated. The new audiological test system according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described. It should also be noted that the accompanying drawings are schematic and simplified for clarity, and they merely show details which are essential to the understanding of the new audiological test system, while other details have been left out.

As used herein, the singular forms "a," "an," and "the" refer to one or more than one, unless the context clearly dictates otherwise.

Figure 1:
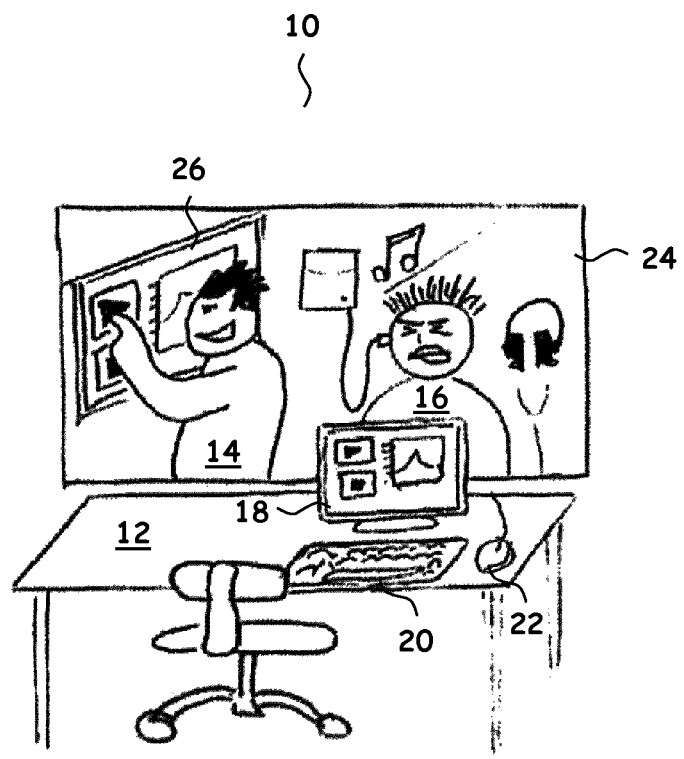
FIGS. 1-7 schematically illustrate an exemplary work flow of performing audiological tests with a prior art PC-based audiological test system, FIGS. 8-12 schematically illustrate an exemplary work flow of performing audiological tests with the new audiological test system.

FIG. 1 schematically illustrates a prior art PC-based audiological test system 10 wherein the Personal Computer (PC) (not shown) is situated at a desk 12 which is intended to be the main working place for the operator 14 of the PC-based audiological test system 10 during performance of audiological test(s) on a patient 16. The PC (not shown) has a user interface comprising a computer screen 18, a keyboard 20, and a mouse 22 as is very well known in the art.

Typically, but not necessarily, the audiological tests are performed inside a sound booth with the desk 12 located outside the sound booth. The patient 16 is not able to see what is displayed on the computer screen 18 when seated in the sound booth.

In FIG. 1 a window 24 of the sound booth is schematically illustrated.

A touch screen 26 is also installed inside the sound booth and controlled by the PC (not shown). In FIG. 1, the touch screen 26 is wall mounted.

In the known PC-based audiological test system 10, the operator 14 invokes the operating system of the PC, e.g. Windows®, to set-up how the PC controls two computer monitors, namely the computer screen 18 and the touch screen 26. The operating system allows two monitor modes, the "duplicate monitor mode" and the "extended monitor mode".

In the "duplicated monitor mode", as is well-known in the art, the PC displays the same information with the same layout in the computer screen 18 and the touch screen 26, i.e. one of the screens 18, 26 shows a duplicate of what the other screen 26, 18 shows.

In the "extended monitor mode", as is well-known in the art, the PC controls the computer screen 18 and the touch screen 26 individually so that the software executed on the PC and the operator of the PC can individually control what information is displayed on the computer screen 18 and what information is displayed on the touch screen 26.

Thus, during performance of audiological tests with the prior art PC-based audiological test system 10, the operator of the prior art PC-based audiological test system 10 has to go to the desk 12 from time to time to invoke the operating system of the PC (not shown) to switch between the "duplicated monitor mode" and the "extended monitor mode" as the requirements of what to display on the touch screen 26 changes between the various types of audiological tests.

In this way, the PC (not shown) is adapted to selectively control the touch screen 26 so that the operator 14 of the PC-based audiological test system 10 can control different features of the audiological test software executed by the PC from inside the sound booth depending on the current set-up of the PC.

The PC (not shown) is also adapted to selectively control the touch screen 26 so that the touch screen 26 can be used for presenting visual stimuli, such as video, to the patient 16.

The PC (not shown) is also adapted to selectively control the touch screen 26 so that the touch screen 26 can be used by the patient 16 to enter response alternatives or enter ratings, e.g. on visual analogue scales.

As schematically illustrated in FIG. 1, some of the audiological tests require that the operator 14 is close to the patient 16, e.g. in order to perform tympanometry. In such cases, the PC is set to the "duplicate monitor mode" for duplicate control of the touch screen 26 inside the sound booth and the computer screen 18 outside the sound booth. However, the operator 14 may recognize, e.g. after having positioned an ear probe appropriately in the desired ear of the patient, that he or she has not selected the correct monitor mode of the PC. Conventionally, the operator 14 in this situation has to move away from the patient to the desk 12 with the computer screen 18 and invoke the operating system of the PC to perform selection of the "duplicate monitor mode". Upon returning to the sound booth, the operator typically has to check or even re-establish the desired positioning of the ear probe in the selected ear of the patient. However, this is not desirable. The operator 14 desires to maintain focus on the patient and the patient's reactions and wants to minimize disturbing activities, such as moving away from the patient.

When pure tone audiometry, the most common audiological test, is performed, it is imperative that the patient 16 does not receive any visual clues that may reveal whether or not the operator 14 presents a pure tone to the patient 16, and/or at what level the pure tone is presented. The operator 14 performs pure tone audiometry from the desk 12 and controls when, and at what frequency, and at what level, to present a pure tone to the patient 16 with the user interface of the PC, including the computer screen 18 as is well-known in the art of pure tone audiometry. Thus, during performance of pure tone audiometry, the PC must not duplicate what is displayed on the computer screen 18 onto the touch screen 26.

Typically, the operator 14 of the prior art PC-based audiological test system 10 simply turns off the touch screen 26 inside the sound booth to make sure that the patient 16 does not receive any visual indications on when the operator 14 presents a pure to the patient 16.

Alternatively, the operator 14 of the prior art PC-based audiological test system 10 may invoke the operating system of the PC to switch the monitor mode to the "extended monitor mode" and control the touch screen 26 to display something that does not include any visual indications on when the operator 14 presents a pure to the patient 16, such as a black screen, a still image, etc.

Figure 2:
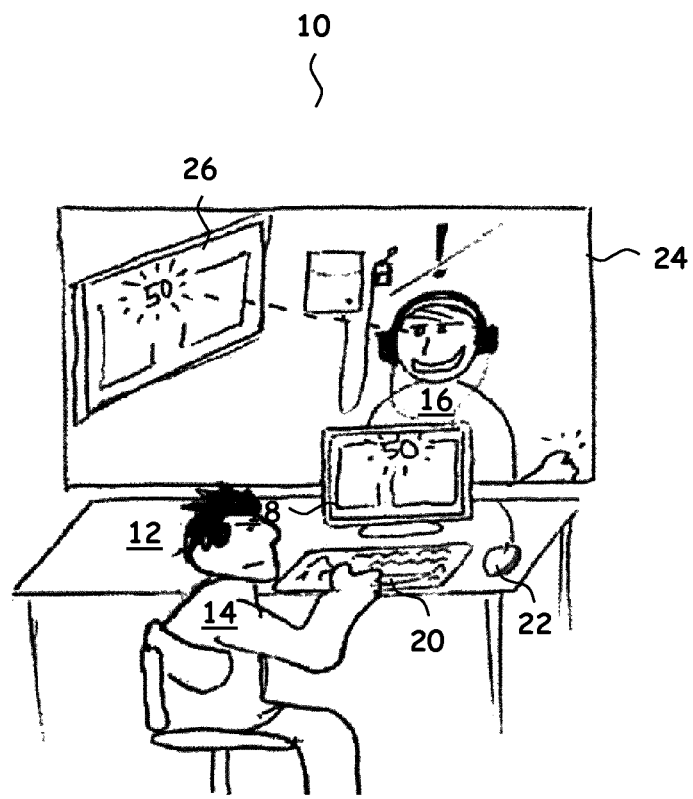

FIG. 2 schematically illustrates what should not happen during a pure tone audiometry test, namely that the PC is inadvertently set to the "duplicate monitor mode" so that, inadvertently, the patient 16 does indeed receive visual cues from the touch screen 26, e.g. when a pure tone is presented during the test. For example, the operator 14 of the an audiological test system may recognize, after having been seated at the desk 12 that he or she did not turn the touch screen 26 off before leaving the sound booth.

Figure 3:
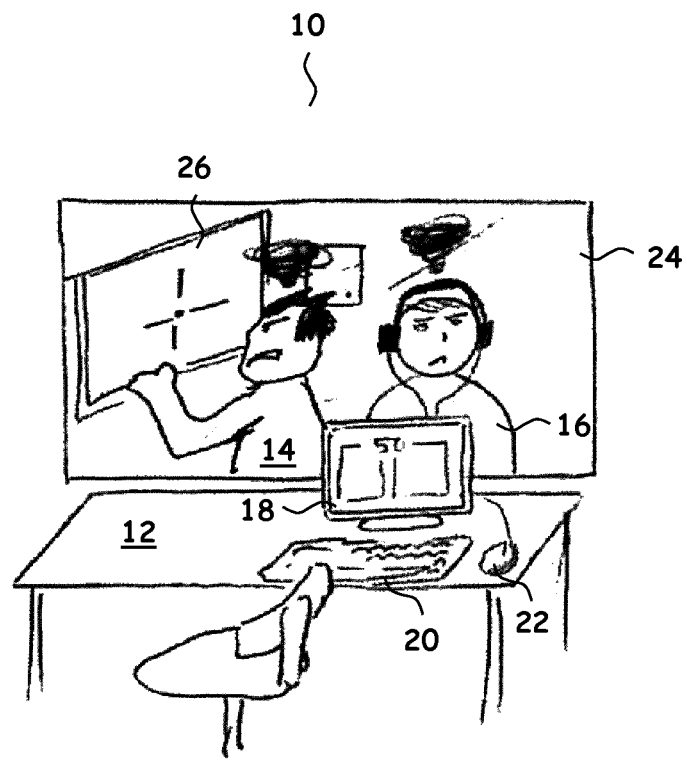

FIG. 3 schematically illustrates how the operator 14 has to go back into the sound booth to switch off the touch screen 26 to make certain that the touch screen 26 does not present visual cues to the patient that may lead to false responses to the next audiological test. Alternatively, the operator 14 has to invoke the operating system of the PC to toggle the monitor mode to the "extended monitor mode". Today, it is most common to turn off the touch screen 26.

Figure 4:
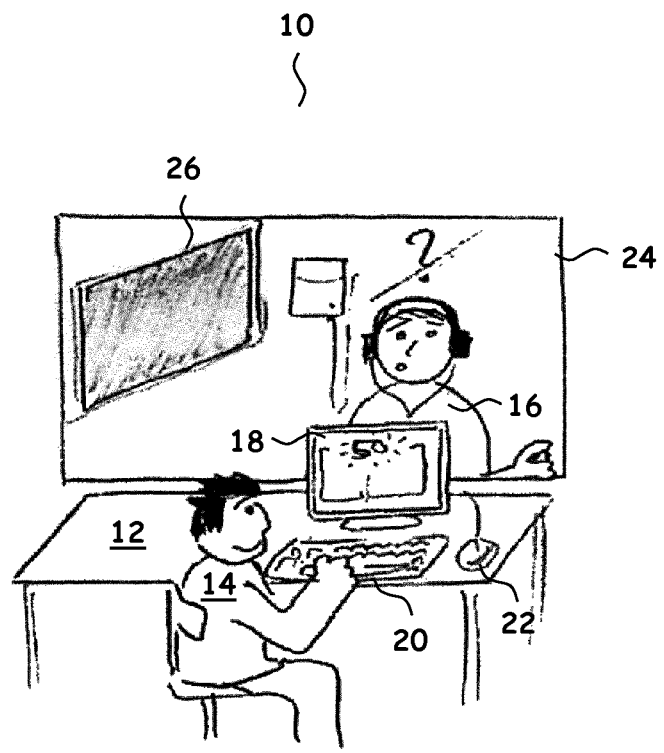

FIG. 4 schematically illustrates that the touch screen 26 has been turned off and presents a black screen to the patient 16. The pure tone audiometry test is in progress without the patient 16 being presented with visual cues on when the operator 14 presents a tone.

Figure 5:
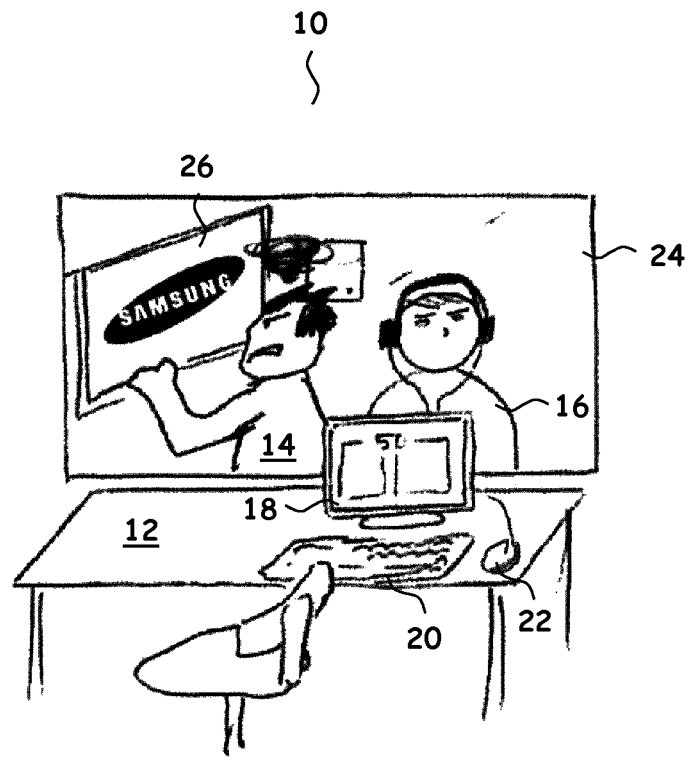

FIG. 5 schematically illustrates that the operator 14 has to enter the sound booth again to switch on the touch screen 26 in order to use the touch screen 26 to present video stimulus to the patient 16.

Figure 6:
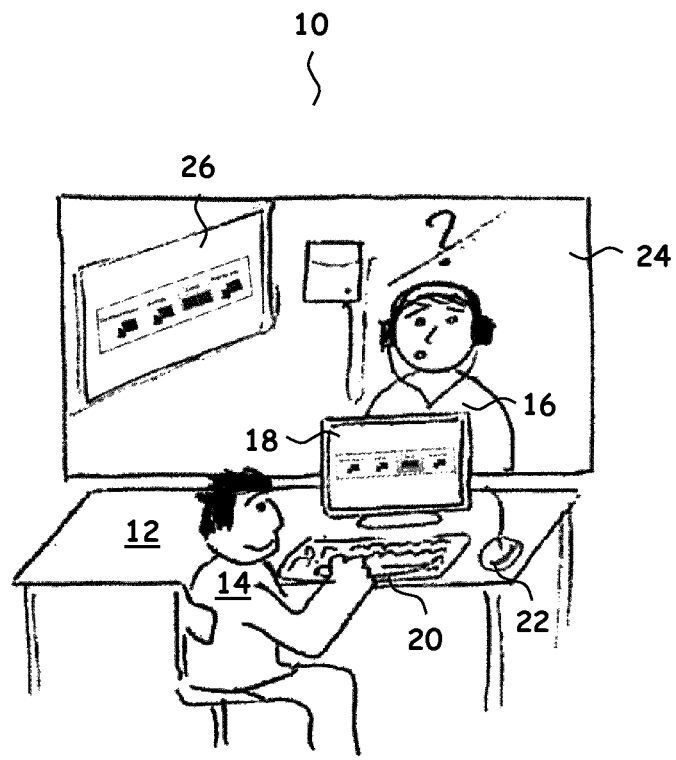

FIG. 6 schematically illustrates that the operator 14 then has to go back to the desk 12 to invoke the operating system of the PC to make sure that the "extended monitor mode" is selected and not the "duplicate monitor mode" in order to use the touch screen 26 to present video to the patient 16 inside the sound booth.

Figure 7:
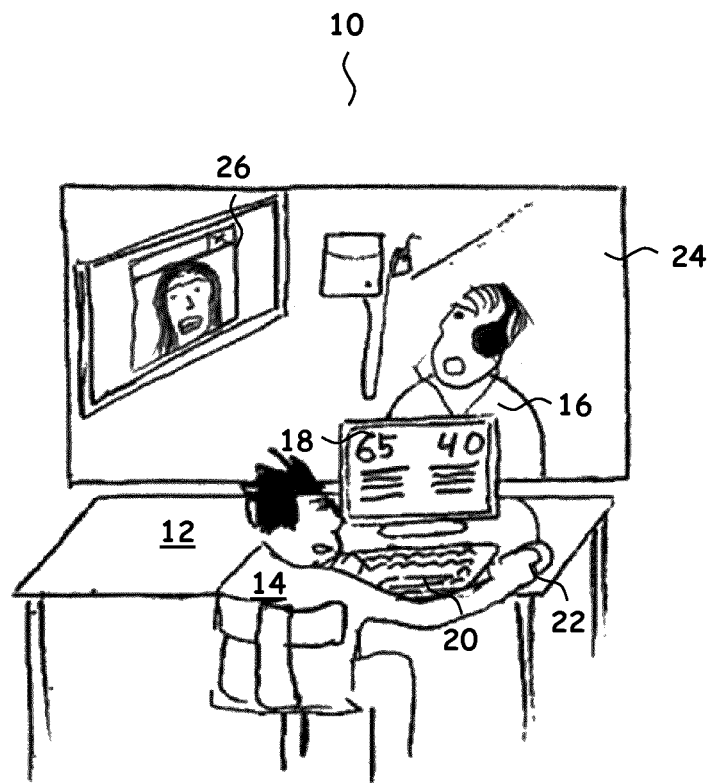

FIG. 7 schematically illustrates that a lip read test is performed using the touch screen 26 to present video stimulus to the patient 16.

In summary, FIGS. 1-7 illustrate how the prior art PC-based audiological test system 10 requires the operator 14 to perform the task of maintaining a part of his or her attention to the fact which monitor mode the PC is currently set to in order to make sure that the touch screen 26 only presents the desired information to the patient 16. The operator 14 is required to invoke the operating system of the PC to set the desired monitor mode instead of maintaining his or her mental attention to the audiological tests and the patient. This distracts the operator 14 from the primary tasks of correctly preparing and performing the desired audiological tests and disrupts the operator work flow of the tests. This makes the audiological tests more time consuming and increases the risk of errors.

In a new PC-based audiological test system 10 according to the appended set of claims, the PC is set to the "extended monitor mode" whenever the audiological test software is executed by the PC so that the first display screen 18, namely the computer screen 18 in FIGS. 8-12, and the second display screen 26, namely the touch screen 26 in FIGS. 8-12, can display different information to the operator 14 and the patient 16, respectively. For example, when performing a video lip-reading test, a separate window is opened in the touch screen 26 for display of the lip-reading test video to the patient 16 inside the sound booth.

In the exemplary new PC-based audiological test system 10 according to the appended set of claims shown in FIGS. 8-12, icon 28 is displayed on the second display screen 26 and icon 30 is displayed on the first display screen 18, and the areas at the respective icons 30, 28 constitute the first and the second switch, respectively.

In the illustrated example, touching the icon 28 on the touch screen 26 will duplicate or move what is displayed on the computer screen 28 onto the touch screen 26, whereby the operator 14 can control the audiologic test system with the touch screen 26 inside the sound booth so that the operator 14 is relieved from the task of the leaving the sound booth during preparation or conductance of audiological tests that require the operator 14 to be close to the patient 16 as for example when preparing and performing tympanometry.

Likewise, using the mouse 22 with a screen cursor to click on the corresponding icon 30 on the computer screen 18 will remove the duplicate display, or move what is displayed from the touch screen to the computer screen 26 so that the patient 16 is not presented with visual information on tasks performed by the operator 14 at the desk 12.

In this way, the operator can select to control the operation of the new audiological test system 10 from the touch screen 26 inside the sound booth; or, from the computer screen 18 outside the sound booth at the desk 12. The operator selection is performed by the operator pressing of clicking on the respective icon 28, 30 on the display screen 18, 26 that the operator desires to control the audiological test system 10 from, and the operator 14 does not need to re-configure or switch off the touch screen 26 at any time.

Figure 8:
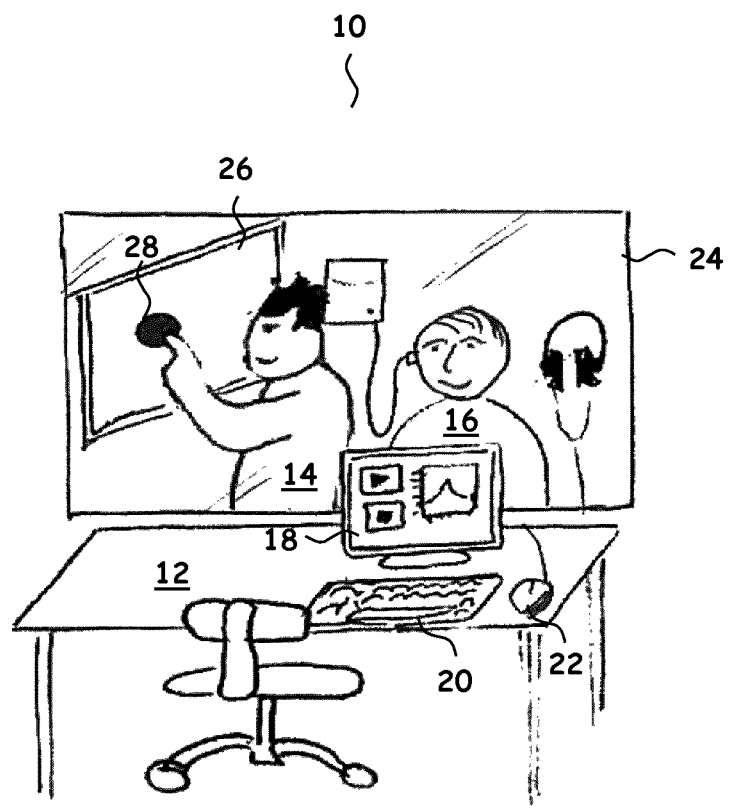

FIG. 8 schematically illustrates an audiological test where the operator needs to be close to the patient, e.g. in order to position an ear probe appropriately in a desired ear of the patient 16 and to be able to record the test results together with identification of the selected ear, e.g. when performing tympanometry. FIG. 8 illustrates that the operator 14 touches the icon 28, illustrated as a circle, on the touch screen 26 to duplicate, or move, to the touch screen 26 what is otherwise displayed to the operator 14 on the computer screen 18 by the audiological test software.

Figure 9:
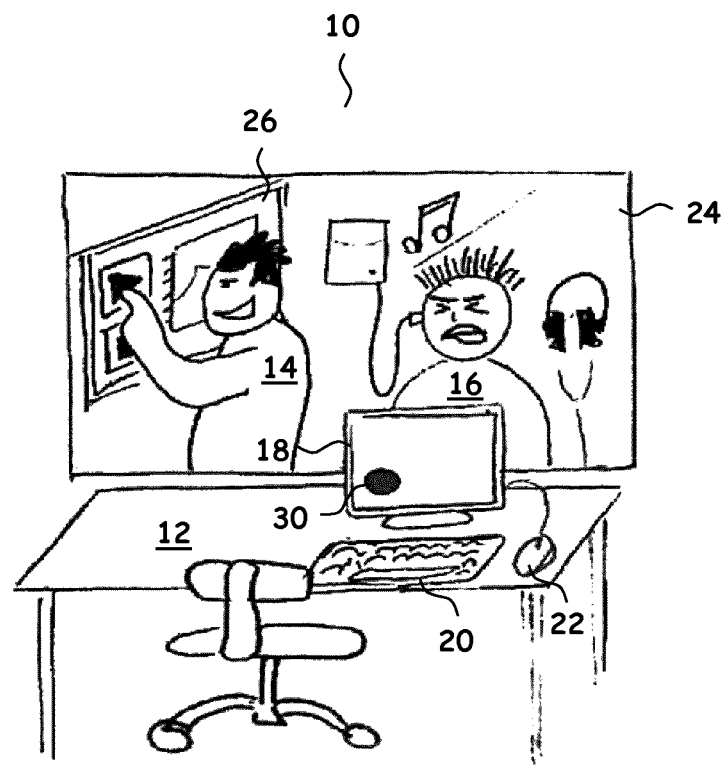

Subsequently, as schematically illustrated in FIG. 9, the operator 14 controls the audiological test system 10 utilizing the touch screen 26. In FIG. 9, what is otherwise displayed to the operator 14 on the computer screen 18 by the audiological test software has been moved to the touch screen 26. An icon 30, illustrated as a circle, is displayed on the computer screen 18. If the operator 14 clicks on the icon 30, the control panel displayed on the touch screen 26 is moved back for display on the computer screen 18, and the touch screen 26 does not duplicate what is displayed on the computer screen 18.

Figure 10:
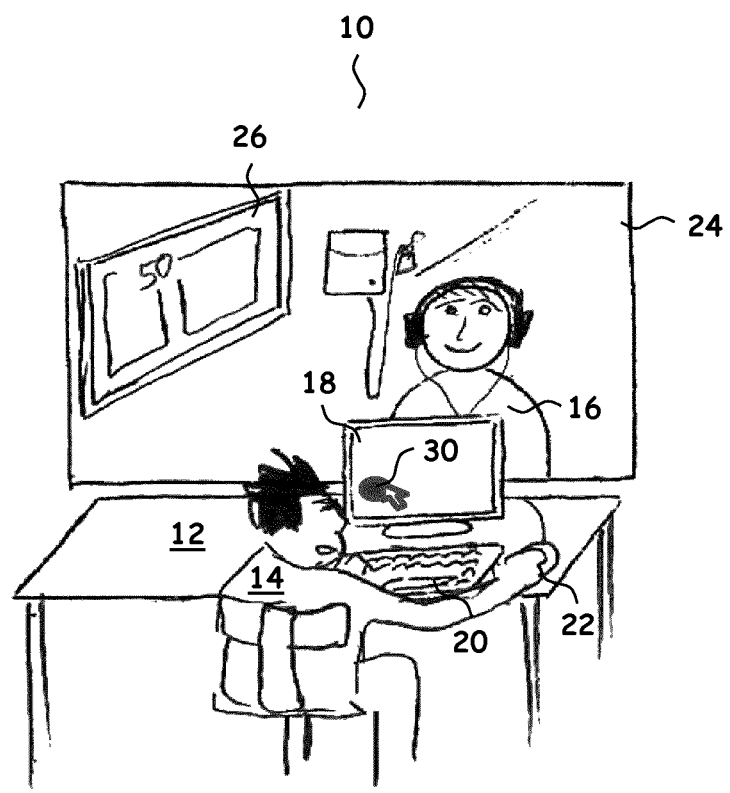

FIG. 10 schematically illustrates performing the next audiological test, e.g. pure tone audiometry. However, during pure tone audiometry, it is imperative that the patient 16 does not receive visual cues from the touch screen 26. The operator 14 uses the mouse 22 and a cursor (not shown) in a way well-known in the art to click on the icon 30 to move the control panel displayed on the touch screen 26 back to the computer screen 18.

Figure 11:
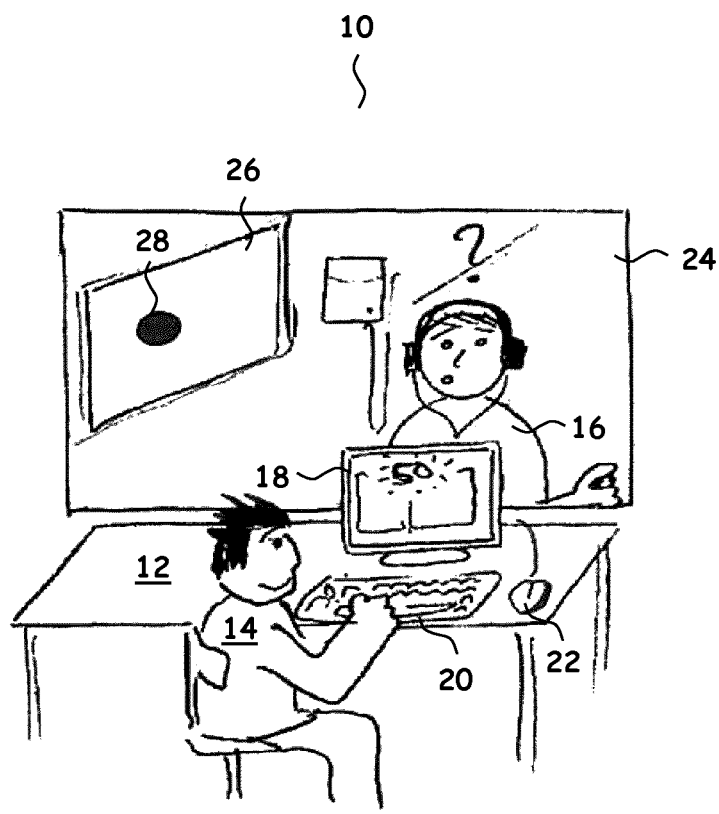

FIG. 11 schematically illustrates an audiological test in progress, in the illustrated example pure tone audiometry, where the patient 16 must not receive visual cues from the touch screen 26 on when the operator 14 presents a pure tone to the patient 16.

In the illustrated example, the touch screen 26 solely displays the icon 28 that makes it possible for the operator 14 to go to the touch screen 26 and move or duplicate to the touch screen 26 what is currently displayed to the operator 14 on the computer screen 18 by the audiological test software.

Figure 12:
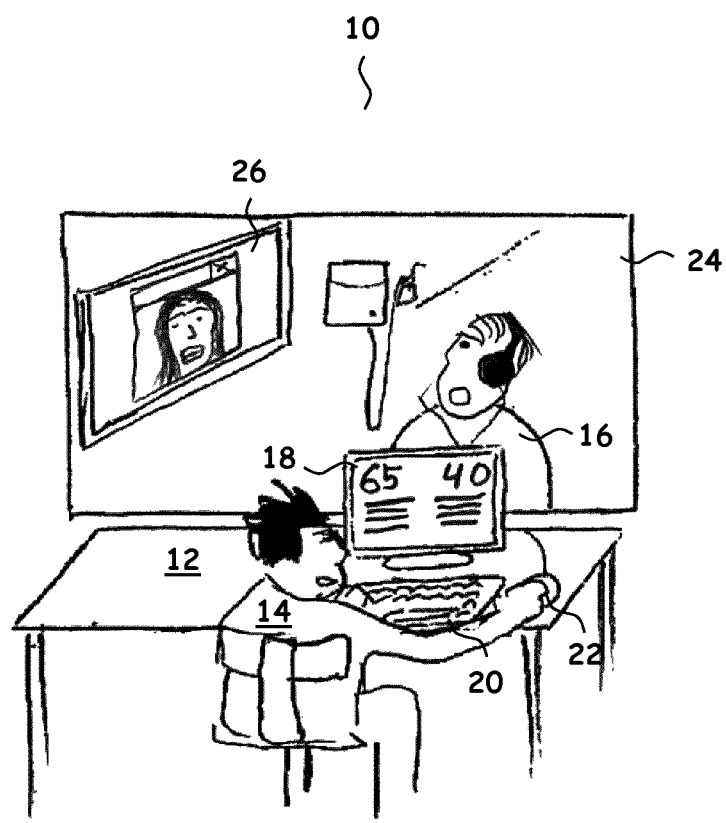
Figure 13:
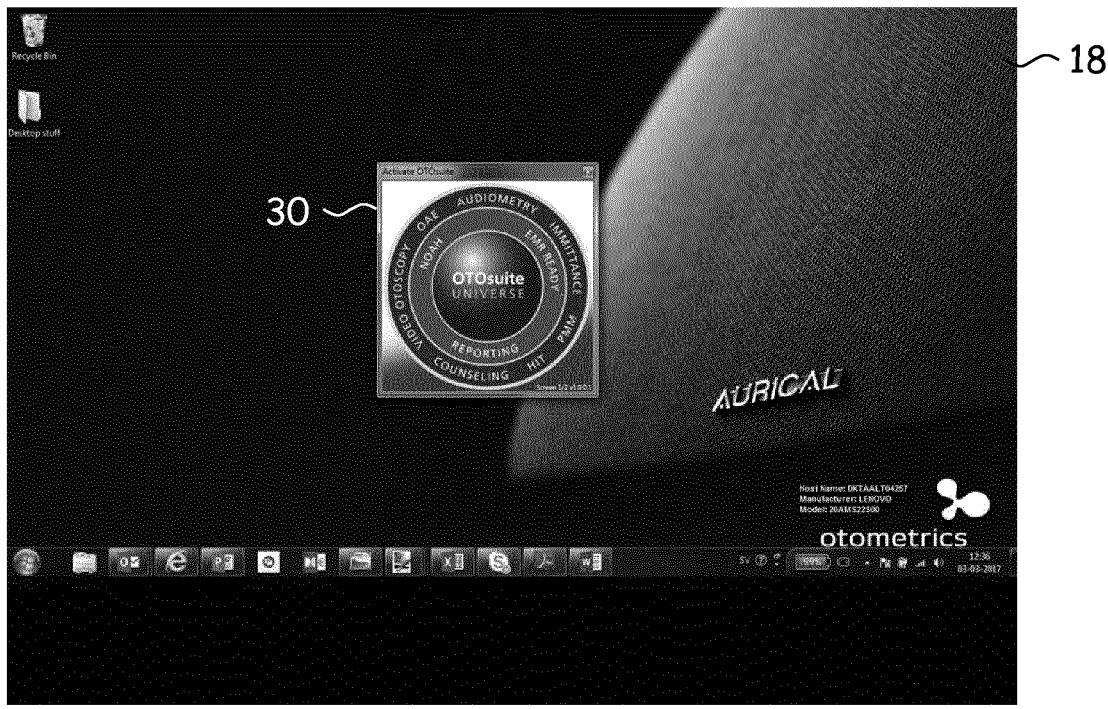
Figure 13:
Figure 14:
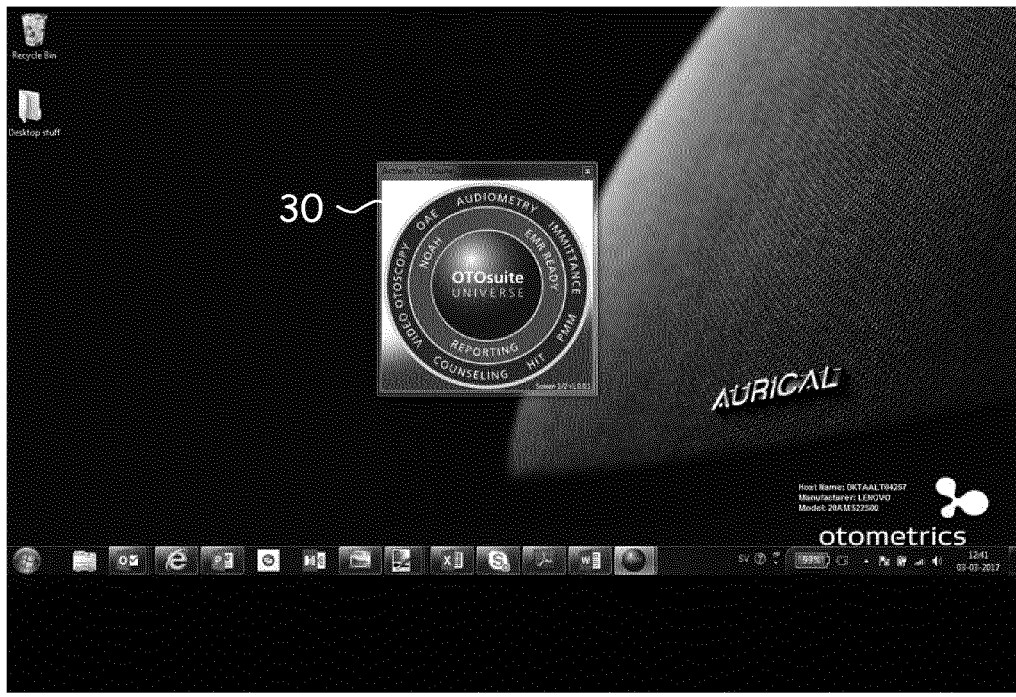
Figure 14:
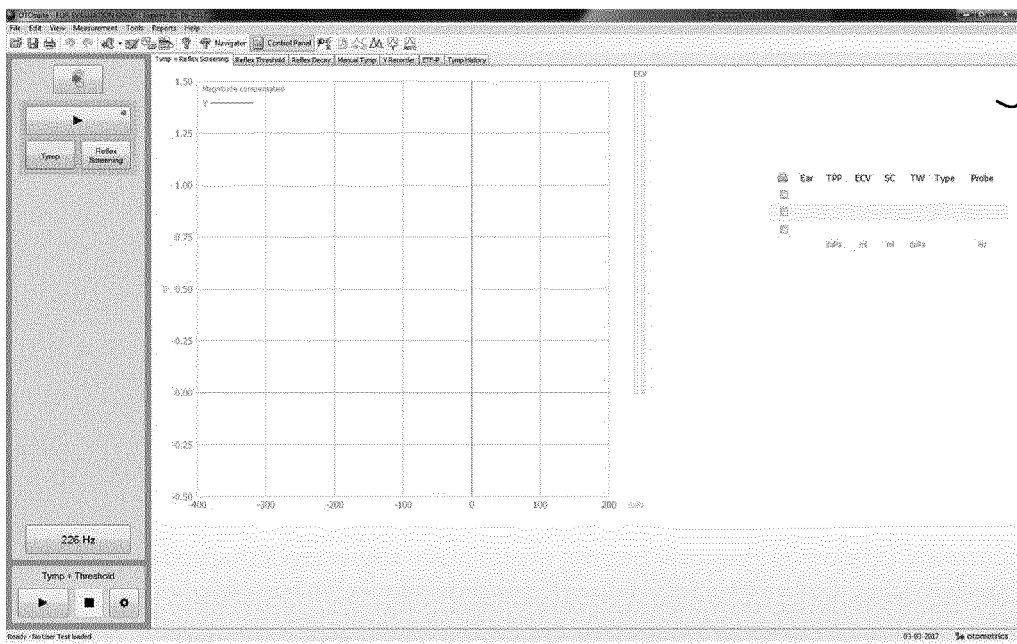
Figure 15:
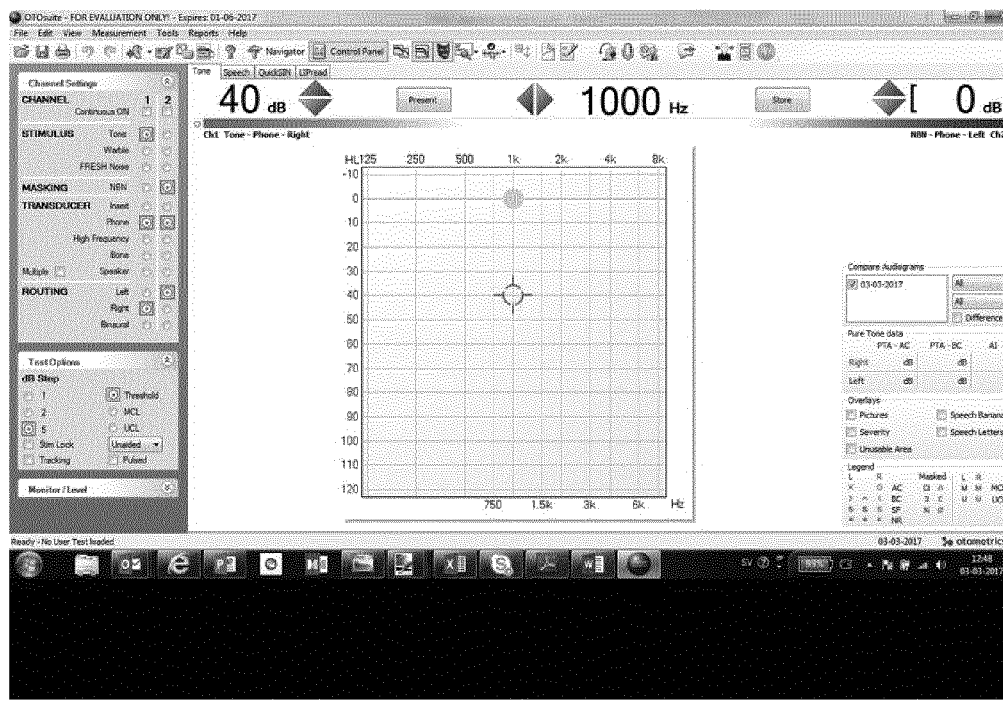
Figure 15:
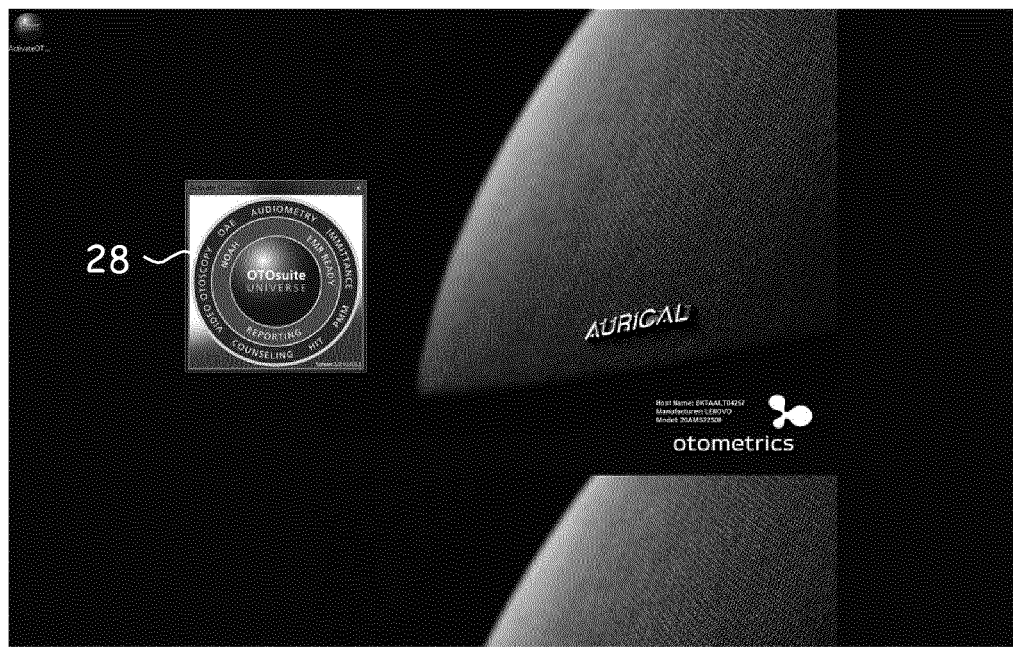
Figure 16:
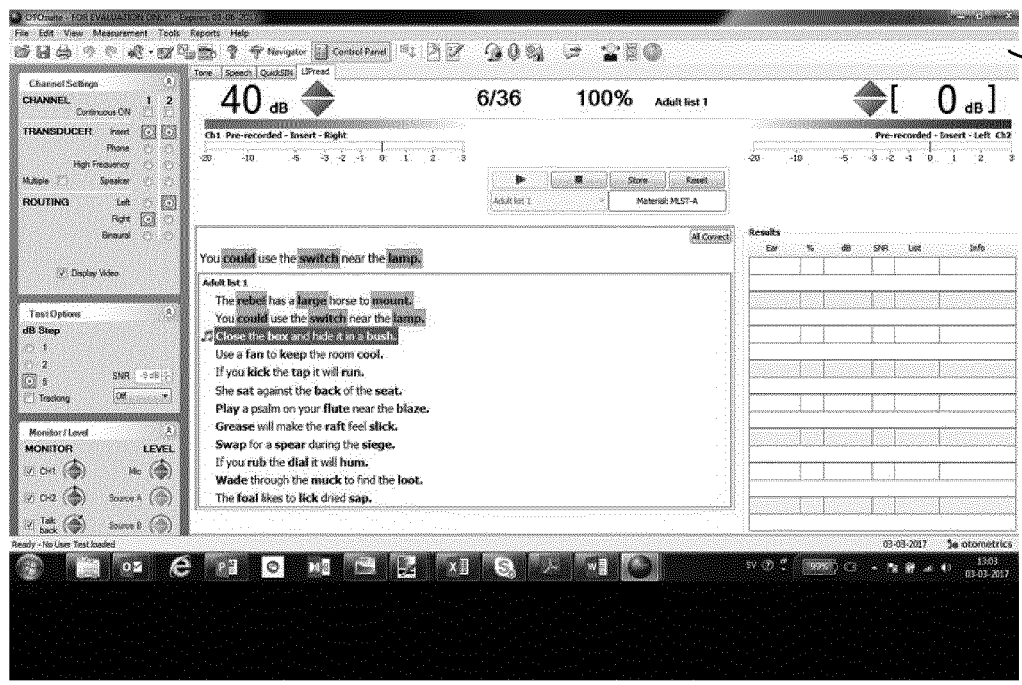
Figure 16:
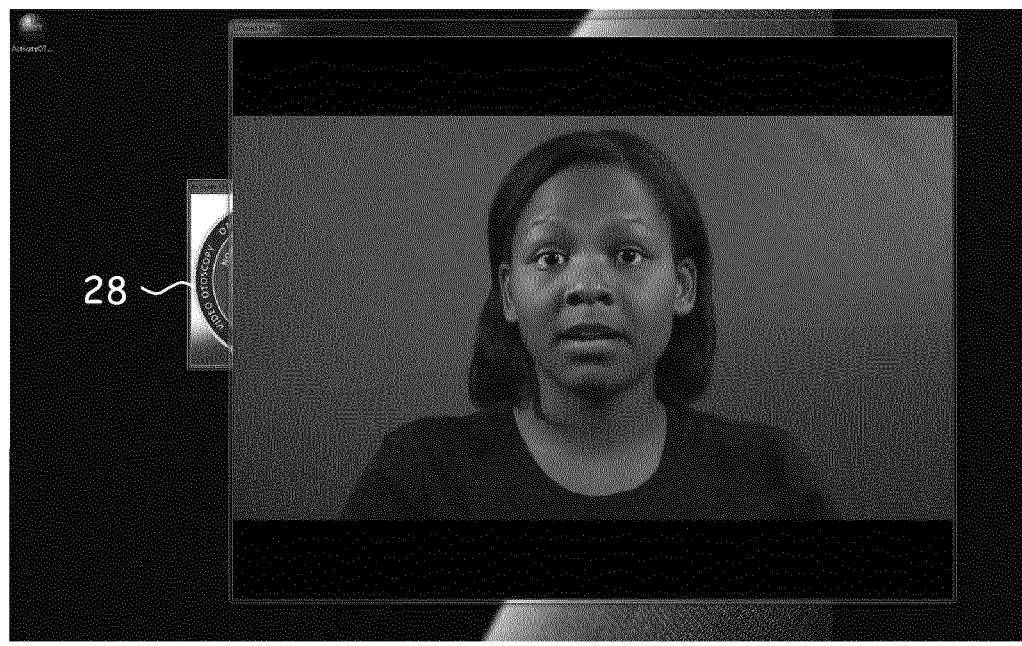

FIG. 12 schematically illustrates an audiological test, e.g. a lip reading test, where the touch screen 26 in the sound booth is used to present video to the patient 16. The test can be started without requiring the operator to interrupt the work flow of audiological testing, e.g. by leaving the desk in order to turn-on the touch screen 26, or by invoking the operating system of the PC to change monitor mode setting.

FIGS. 13A-16B show various exemplary screen dumps of the computer screen 18 and the touch screen 26 of the new audiological test system.

FIG. 13A-B show a screen dump of the computer screen 18 (FIG. 13A) and of the touch screen 26 (FIG. 13B) before the operator of the system has launched the audiological test software.

In the illustrated example, touching the icon 28 on the touch screen 26 will open the audiological test software on the touch screen 26, i.e. a graphical user interface of the audiological test software will be displayed on the touch screen 26, whereby the operator (not shown) can control the audiologic test system with the touch screen 26 inside the sound booth so that the operator is relieved from the task of the leaving the sound booth during preparation or conductance of audiological tests that require the operator to be close to the patient (not shown) as for example when preparing and performing tympanometry.

Likewise, using a mouse (not shown) with a screen cursor (not shown) to click on the corresponding icon 30 on the computer screen 18 will open the audiological test software on the computer screen 18, i.e. a graphical user interface of the audiological test software will be displayed on the computer screen 26 so that the patient is not presented with visual information on tasks performed by the operator.

In this way, the operator can select to control the operation of the new audiological test system 10 from the touch screen 26 inside the sound booth (not shown); or, from the computer screen 18 outside the sound booth at the desk (not shown). The operator selection is performed by the operator pressing of clicking on the respective icon 28, 30 of the respective one of the computer screen 18 and the touch screen 26 that the operator desires to control the audiological test system 10 from, and the operator does not need to re-configure or switch off the touch screen 26 at any time.

In FIGS. 14A and B, the operator has opened the audiological test software on the touch screen 26.

In FIGS. 15A and B, the operator has opened the audiological test software on the computer screen 18.

In FIGS. 16A and B, the operator has opened the audiological test software on the computer screen 18 and has selected a lip-reading test wherein the PC of the audiological test system controls the touch screen 26 to show a lip-reading test video with a speaking person to be lip-read by the patient.

Thus, in summary, with the new audiological test system according to the appended set of claims, the operator 14 never has to worry about the current state of the touch screen 26 in the sound booth. Further, the operator 14 can control the audiological test system 10 from the computer screen 18 or the touch screen 26 as desired. The operator 14 may simply touch or click on the icon 28, 30 displayed on the respective display screen 28, 26 from which the operator 14 desires to control the audiological test system 10. In this way, the operator 14 saves time and effort and the risk of errors is decreased. The operator 14 is relieved from the task of maintaining part of his or her attention on which monitor mode the audiological test system is currently set to, and from having to invoke an operating system of the audiological test system to set the desired monitor mode. Instead, the operator 14 is allowed to focus on the primary tasks of correctly preparing and performing the desired audiological tests.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. An audiological test system for audiological testing of a patient situated at a test location, comprising:
   a first display screen positioned outside a viewing field of the patient when the patient is situated at the test location;
   a second display screen positioned within the viewing field of the patient when the patient is situated at the test location;
   a computerized device directly connected to each of the first display screen and the second display screen, comprising:
   a processor; and
   a memory unit comprising a user interface application executable by the processor, the user interface application comprising:
      an input module configured to receive an input from an operator; and
      a display management module configured to control the display of information of the audiological test on the first display screen and the second display screen based on the input from the input module;
   a first switch located at the first display screen and adapted for control of the first and second display screens in such a way that predetermined information relating to operation of the audiological test system is displayed on the first display screen and not displayed on the second display screen upon activation of the first switch, and a second switch located at the second display screen and adapted for control of the first and second display screens in such a way that the predetermined information relating to operation of the audiological test system is displayed on the second display screen and not displayed on the first display screen upon activation of the second switch;

wherein the input module is configured to receive an input from the operator via a user interface connected to the computerized device.

2. The audiological test system of claim 1 wherein the computerized device further comprises:

a first user interface device configured to provide a first user input; and a second user interface device configured to provide a second user input.

3. The audiological test system according to claim 2, wherein the first display screen is a first touch screen and the first touch screen constitutes the first user interface device.

4. The audiological test system according to claim 3, wherein the first switch is constituted by a specific touch sensitive area of the first touch screen.

5. The audiological test system according to claim 2, wherein the second display screen is a second touch screen and the second touch screen constitutes the second user interface device.

6. The audiological test system according to claim 5, wherein the second switch is constituted by a specific touch sensitive area of the second touch screen.

7. The audiological test system according claim 1, wherein the first switch accommodates an indicator for indication of whether the predetermined information relating to operation of the audiological test system is displayed or not displayed on the second display screen.

8. An audiological test system comprising a user interface, comprising:

a first display screen configured to display information of an audiological test to an operator, the first display screen positioned such that a patient cannot view the information displayed thereon;

a second display screen configured and positioned to display information of the audiological test to the patient;

a first switch configured to control the display of information of the audiological test on the first and second display screens in such a way that predetermined information relating to operation of the audiological test system is displayed on the first display screen and not displayed on the second display screen upon activation of the first switch, the first switch positioned at the first display screen;

a second switch configured to control the display of information of the audiological test on the first and second display screens in such a way that the predetermined information relating to operation of the audiological test system is displayed on the second display screen and not displayed on the first display screen upon activation of the second switch, the second switch positioned at the second display screen; and a user interface server directly connected to each of the first display screen and the second display screen, the user interface server residing on a central computer having a processor installed with a user interface application and coupled with a memory unit integrated with a central database, the user interface server comprising:

an input module, at the processor, being configured to receive an input from the operator; and a display management module, at the processor, being configured to control the display of information of the audiological test on the first display screen and the second display screen based on the input from the input module.

9. The user interface system of claim 8 wherein the user interface server facilitates control of the first display screen and the second display screen.

10. The user interface system of claim 8 wherein the first switch and the second switch are each a conventional mechanical switch.

11. The user interface system of claim 10 wherein the first switch and the second switch are an icon displayed on the first display screen and the second display screen respectively.

12. The user interface system of claim 11 wherein the first switch and the second switch can be activated by the positioning of a cursor on top of the icon and clicking on it using a mouse, a trackball, or a touchpad.

13. The user interface system of claim 8 wherein the user interface can simultaneously display different information on the first display screen and the second display screen.

14. The audiological test system of claim 8 further comprising:

a first user interface device configured to provide a first user input to the user interface server; and a second user interface device configured to provide a second user input to the user interface server.

15. A method for utilizing an audiological test system comprising a user interface for selectively displaying information regarding an audiologic test system to an operator and a patient, the method comprising the steps of:

positioning a first display screen to display information of the audiological test to an operator such that the patient cannot view the information displayed thereon;

positioning a second display screen to display information of the audiological test to the patient such that the patient can view the information thereon;

directly connecting each of the first display screen and the second display screen to a computerized device configured to control the display of information on each of the first display screen and the second display screen;

activating a first switch allowing the operator to display information relating to operation of the audiological test system on the first display screen and not to display information relating to operation of the audiological test system on the second display screen; and activating a second switch by the operator to display information relating to operation of the audiological test system on the second display screen and not to display information relating to operation of the audiological test system on the first display screen.

16. The method of claim 15 wherein different information can be displayed on the first display screen and the second display screen.

17. The method of claim 15 wherein the first display screen and the second display screen are placed at a distance so they cannot be viewed simultaneously from a test location used for audiological testing of a patient.

18. The method of claim 15 wherein the operator need not turn off the second display screen next to the patient to ensure the patient does not receive any visual cues relating to the audiological test.

19. The method of claim 15 wherein the first switch and the second switch are an icon displayed on the first display screen and the second display screen respectively.

20. The method of claim 19 wherein:
activation of the first switch comprises receiving a user input from a first user input device selecting the icon on the first display screen; and
activation of the second switch comprises receiving a user input from a second user input device selecting the icon on the second display screen.

* * * * *